United States Patent
Tsuzaki et al.

(10) Patent No.: US 9,638,371 B2
(45) Date of Patent: May 2, 2017

(54) STORAGE METHOD FOR TRIFLUOROETHYLENE, AND STORAGE CONTAINER FOR TRIFLUOROETHYLENE

(71) Applicant: ASAHI GLASS COMPANY, LIMITED, Chiyoda-ku (JP)

(72) Inventors: Masaaki Tsuzaki, Chiyoda-ku (JP); Masato Fukushima, Chiyoda-ku (JP); Maki Shigematsu, Chiyoda-ku (JP)

(73) Assignee: Asahi Glass Company, Limited, Chiyoda-ku (JP)

( * ) Notice: Subject to any disclaimer, the term of this patent is extended or adjusted under 35 U.S.C. 154(b) by 0 days.

(21) Appl. No.: 14/995,566

(22) Filed: Jan. 14, 2016

(65) Prior Publication Data

US 2016/0123534 A1 May 5, 2016

Related U.S. Application Data

(63) Continuation of application No. PCT/JP2014/068477, filed on Jul. 10, 2014.

(30) Foreign Application Priority Data

Jul. 16, 2013 (JP) ................................ 2013-147575

(51) Int. Cl.
*F17C 5/02* (2006.01)
*F17C 1/00* (2006.01)
*C07C 21/18* (2006.01)

(52) U.S. Cl.
CPC ................ *F17C 5/02* (2013.01); *C07C 21/18* (2013.01); *F17C 1/00* (2013.01); *F17C 2221/038* (2013.01); *F17C 2270/01* (2013.01)

(58) Field of Classification Search
CPC .... F17C 5/02; F17C 5/04; F17C 1/005; F17C 1/00; F17C 13/00; F17C 13/001; B65B 31/00; C07C 21/18
USPC ................ 220/581, 560.12, 560.04; 206/0.6; 53/432; 141/7, 8
See application file for complete search history.

(56) References Cited

U.S. PATENT DOCUMENTS

| | | | | |
|---|---|---|---|---|
| 4,898,645 A | * | 2/1990 | Voigt | ...................... C07C 17/38 203/67 |
| 8,579,146 B2 | * | 11/2013 | Tatarek | ..................... F17C 1/14 220/586 |
| 2008/0287715 A1 | | 11/2008 | Taguchi et al. | |
| 2011/0034740 A1 | | 2/2011 | Aida et al. | |
| 2011/0079040 A1 | | 4/2011 | Morimoto et al. | |

FOREIGN PATENT DOCUMENTS

| | | |
|---|---|---|
| JP | 2001-240570 | 9/2001 |
| JP | 2008-308480 | 12/2008 |
| JP | 2011-85275 | 4/2011 |
| WO | WO 2009/130986 A1 | 10/2009 |
| WO | WO 2009/157325 A1 | 12/2009 |
| WO | WO 2010/098447 A1 | 9/2010 |
| WO | WO 2010/098451 A1 | 9/2010 |
| WO | WO 2012/157762 A1 | 11/2012 |
| WO | WO 2013/161724 A1 | 10/2013 |

OTHER PUBLICATIONS

Halocarbon. "Trifluoroethylene R-1123". http://www.halocarbon.com/halocarbon_media/MaterialSafetyData_160.pdf, May 23, 2005. pp. 3 and 5.*
International Search Report issued Oct. 28, 2014 in PCT/JP2014/068477 filed Jul. 10, 2014.

* cited by examiner

*Primary Examiner* — Robert J Hicks
(74) *Attorney, Agent, or Firm* — Oblon, McClelland, Maier & Neustadt, L.L.P.

(57) ABSTRACT

To provide a method for storing trifluoroethylene filled in a container for storage, transportation, etc., stably without causing a reaction such as polymerization. The method is characterized in that trifluoroethylene is stored in a sealed container in such a state that a gas phase and a liquid phase coexist, and in the gas phase, the concentration of oxygen at a temperature of 25° C. is kept to be at most 1,000 ppm by volume.

12 Claims, No Drawings

STORAGE METHOD FOR TRIFLUOROETHYLENE, AND STORAGE CONTAINER FOR TRIFLUOROETHYLENE

TECHNICAL FIELD

The present invention relates to a storage method and storage container for trifluoroethylene, particularly to a method for storing trifluoroethylene stably for storage, transportation, etc., and a container in which trifluoroethylene is stably stored.

BACKGROUND ART

Trifluoroethylene ($CF_2$=CHF) is expected as a new refrigerant to replace chlorofluorocarbons (CFC) or hydrochlorofluorocarbons (HCFC) that destroy the ozone layer, or hydrofluorocarbons (HFC) being greenhouse gases.

Such trifluoroethylene is stored or transported as filled in a sealed container under pressure at a temperature of at most normal temperature, or as liquefied and filled in a sealed container under pressure with cooling. Trifluoroethylene filled in a sealed container in such a manner, is in a gas-liquid state having a gas phase and a liquid phase. And, trifluoroethylene in such a gas-liquid state is desired to be kept stably without causing a reaction such as polymerization, in order to maintain the quality as a refrigerant, or to prevent deposition of impurities (solids) in the container.

Fluoroolefins are known to undergo a polymerization reaction if oxygen is present, as the oxygen becomes a radical source. Among such fluoroolefins, tetrafluoroethylene tends to be polymerized in the presence of a very small amount of oxygen at a level of from 1 to a few tens ppm, and in some cases, the polymerization reaction is likely to proceed explosively. For example, Patent Document 1 discloses that tetrafluoroethylene undergoes polymerization at an oxygen concentration of 1.4 ppm to form polytetrafluoroethylene. Therefore, at the time of storing a fluoroolefin, it becomes important to handle it by removing oxygen to the limit.

However, in order to remove oxygen to the limit, it is necessary to take a measure such as providing a new step for removing oxygen to the limit in the production process, whereby the cost associated therewith will be incurred. Further, by conducting the step of removing oxygen to the limit, there may be a case where the yield tends to be low, and the production cost will be increased.

To what extent trifluoroethylene is stable against a self-polymerization reaction in the presence of oxygen, is largely unknown. A method for storing trifluoroethylene without permitting it to undergo a polymerization reaction, is desired, in order to maintain its quality as a refrigerant and to carry out its storage and transportation inexpensively, safely and stably.

Heretofore, for stabilization of hydrofluoroolefins, some proposals have been made. Patent Document 2 has proposed a method of adding a stabilizer such as an alkyl catechol or an alkoxy phenol, in order to maintain the stable state (state without formation of an acid) of hydrofluoropropene even in the presence of air. Further, Patent Document 3 discloses a stabilization method of adding a $C_{1-4}$ aliphatic alcohol as a stabilizer to hydrofluoropropene.

However, each of such methods disclosed in Patent Document 2 and Patent Document 3 presupposes the existence of a refrigerating machine oil, and it is a method of stabilizing the overall cooling system by stabilizing the refrigerant composition, wherein the conditions are different from stabilization of a refrigerant in a container for storage or transportation, and therefore, it is difficult to apply such a method to store a refrigerant in a container. Further, in the method of adding a stabilizer, it is required to remove the stabilizer prior to use as a refrigerant, whereby not only the load of the process is large, but also there may be a case where the stabilizer cannot be completely removed by a physical purification method such as distillation, such being undesirable from the viewpoint of quality control.

PRIOR ART DOCUMENTS

Patent Documents

Patent Document 1: JP-A-2008-308480
Patent Document 2: WO2010/098451
Patent Document 3: WO2010/098447

DISCLOSURE OF INVENTION

Technical Problem

The present invention has been made to overcome the above problem, and it is an object of the present invention to provide a method for storing trifluoroethylene filled in a container for storage or transportation, inexpensively and stably without causing a reaction such as polymerization, and a container in which trifluoroethylene is stably stored.

Solution to Problem

The storage method for trifluoroethylene of the present invention comprises storing trifluoroethylene in a sealed container and is characterized in that in the sealed container, trifluoroethylene is stored in such a state that a gas phase and a liquid phase coexist, and the concentration of oxygen in the gas phase at a temperature of 25° C. is kept to be at most 1,000 ppm by volume.

In the storage method for trifluoroethylene of the present invention, said concentration of oxygen is kept to be preferably from 1 to 1,000 ppm by volume, more preferably from 3 to 1,000 ppm by volume, further preferably from 3 to 300 ppm by volume, most preferably from 3 to 50 ppm by volume.

The storage container for trifluoroethylene of the present invention is a sealed storage container in which trifluoroethylene is filled in such a state that a gas phase and a liquid phase coexist, and the concentration of oxygen in the gas phase at a temperature of 25° C. is at most 1,000 ppm by volume.

In the storage container for trifluoroethylene of the present invention, said concentration of oxygen is preferably from 1 to 1,000 ppm by volume, more preferably from 3 to 1,000 ppm by volume, further preferably from 3 to 300 ppm by volume, most preferably from 3 to 50 ppm by volume.

Advantageous Effects of Invention

According to the storage method for trifluoroethylene and the storage container for trifluoroethylene of the present invention, a polymerization reaction or the like of trifluoroethylene is prevented, whereby it is possible to maintain the trifluoroethylene with high purity and high quality. Further, a solid polymerization product will not be formed in the container, whereby there will be no possibility of clogging of the supply valve or contamination to the refrigerating device. Furthermore, according to the storage method for trifluoroethylene and the storage container for trifluoroethylene of the present invention, it is possible to carry out the storage at a low cost.

DESCRIPTION OF EMBODIMENTS

Now, embodiments of the present invention will be described.

Hereinafter, an oxygen concentration in the gas phase of trifluoroethylene is meant for an oxygen concentration in a case where the gas temperature is 25° C.

The present inventors have studied the relationship between the oxygen concentration in trifluoroethylene and the progress of the polymerization, and as a result, have found that in a case where the oxygen concentration in the gas phase is from 0 to 1 ppm by volume, polymerization of trifluoroethylene does not proceed. Based on this finding, it has been made possible to estimate the oxygen concentration at which the polymerization does not proceed to bring about a substantial inconvenience even if the oxygen concentration in the gas phase is higher than 1 ppm by volume. Since the presence of oxygen to a certain extent of the oxygen concentration is allowable, it becomes unnecessary to remove oxygen to the limit near 0 ppm by volume. This makes it possible to reduce the production cost, etc. of trifluoroethylene for storage. By setting the lower limit of the oxygen concentration in the gas phase to be 3 ppm by volume, it is possible to increase the oxygen removing treatment speed and to further reduce the production cost. The upper limit of the allowable oxygen concentration range is at most 1,000 ppm by volume, preferably 300 ppm by volume, more preferably 50 ppm by volume.

The storage method of the present invention is characterized in that trifluoroethylene is stored in a sealed container under pressure in such a state that a gas phase and a liquid phase coexist, and in the gas phase, the concentration of oxygen at a temperature of 25° C. is kept to be at most 1,000 ppm by volume. Here, in the sealed container, trifluoroethylene is kept in a gas-liquid coexistence state, and therefore, in the gas phase, trifluoroethylene exhibits a saturated vapor pressure. The above oxygen concentration may be said to be the content that indicates how much oxygen is contained in the gas phase of trifluoroethylene.

Not infrequently, a part of trifluoroethylene in a storage container is taken out, and thereafter, the rest of trifluoroethylene will be continuously stored in the storage container. In such a case, the volume of the gas phase in the storage container increases, but the concentration of oxygen in the gas phase having the volume increased will be kept to be at most 1,000 ppm by volume. The oxygen concentration in the gas phase is usually in an equilibrium state with the oxygen concentration in trifluoroethylene in the liquid phase, and therefore, it is considered that unless oxygen enters into the storage container when the part of trifluoroethylene is taken out, the oxygen concentration in the gas phase would not substantially increase.

The storage container for trifluoroethylene of the present invention is characterized in that it is a sealed storage container wherein trifluoroethylene is filled in such a state that a gas phase and a liquid phase coexist, and in the gas phase, the oxygen concentration at a temperature of 25° C. is at most 1,000 ppm by volume.

The storage container for trifluoroethylene does not require any special structure or material, so long as it is a sealed container capable of enclosing trifluoroethylene in the gas-liquid coexistence state under internal pressure, and it may have a wide range of forms and functions. For example, a storage tank being a fixed storage container, or a pressure resistant container such as a filling cylinder or a secondary filling cylinder (service can) to be used for transportation, may be mentioned. Further, as the material for the storage container, it is possible to use, for example, carbon steel, manganese steel, chromium-molybdenum steel or other low alloy steel, stainless steel, aluminum alloys, etc.

The oxygen concentration in the gas phase is at most 1,000 ppm by volume. When the oxygen concentration in the gas phase is at most 1,000 ppm by volume, it is possible to sufficiently prevent a reaction such as polymerization of trifluoroethylene in the liquid phase and the gas phase.

The oxygen concentration in the gas phase is preferably from 1 to 1,000 ppm by volume, more preferably from 3 to 1,000 ppm by volume, further preferably from 3 to 300 ppm by volume, most preferably from 3 to 50 ppm by volume.

The oxygen concentration in the gas phase may be attained by pressurizing trifluoroethylene to form a liquid and injecting this liquid into a closed container having the oxygen concentration reduced to at most 1,000 ppm by volume by preliminarily vacuum deaerating air. When the liquid of trifluoroethylene is injected into the container, the space in the container will be quickly saturated by the vapor from the liquid. And, the concentration of oxygen in the gas phase thus filled with saturated vapor of trifluoroethylene becomes to be at most 1,000 ppm by volume.

Here, at the time of deaerating the sealed container, non-condensable gases such as nitrogen may also be removed together with oxygen, and the total content of non-condensable gases at a temperature 25.0° C. is preferably adjusted to be an amount not exceeding 1.5 vol % (i.e. 15,000 ppm by volume).

According to the storage method for trifluoroethylene of the present invention as described above, trifluoroethylene filled in a gas-liquid state in the closed container will not undergo a reaction such as polymerization or the like, whereby it is possible to maintain the purity of trifluoroethylene and the high quality as a refrigerant. Further, no solid polymerization product will be formed in the closed container, whereby clogging of a valve, etc. or contamination to the refrigerating system, is less likely to occur. Further, it is possible to store trifluoroethylene at a low cost.

Evaluation of the storage method of the present invention may be conducted, for example, in such a manner that trifluoroethylene in a gas-liquid state is injected together with a predetermined amount of oxygen into a closed container, and the entirety is heated to a predetermined temperature and held in a constant temperature state for a predetermined time, whereupon reaction products in the liquid phase of trifluoroethylene, will be identified and analyzed. This evaluation corresponds to an accelerated test in which a thermal load is applied. The heating temperature may be set in a range of −70 to 300° C. which is a set temperature range of the constant temperature vessel. Further, the heat treatment time may be optionally set. The identification and analyses of the reaction products may be carried out, for example, by the methods described in Examples given hereinafter.

EXAMPLES

Now, the present invention will be described in detail with reference to Examples, but the present invention is by no means limited to the following Examples. Ex. 1 to 7 and 11 are Examples of the present invention, and Ex. 8 to 10 and 12 are Comparative Examples.

Ex. 1 to 10

In a SUS316 pressure-resistant container having an internal volume of 200 cc (maximum operating temperature: 300° C., the maximum working pressure: 20 MPa), a tube made of Pyrex (registered trademark) having the weight preliminarily measured, was inserted. The pressure-resistant container was sealed, and inside of the container was evacuated. Here, the tube was inserted to confirm the presence or absence of formation of a polymer in the pressure-resistant test container.

Then, a predetermined amount of oxygen is introduced into the pressure-resistant container, and 100 g of liquefied trifluoroethylene having a purity of 99.5% was filled to bring the oxygen concentration in the gas phase to have the value shown in Table 1 at 25° C.

Then, the pressure-resistant container having trifluoroethylene thus sealed-in together with oxygen having a predetermined concentration, was placed in a hot air circulating constant temperature vessel and left to stand in a constant temperature state of 60° C. for 20 days.

Upon expiration of the 20 days, the pressure-resistant container was taken out from the constant temperature vessel, and trifluoroethylene was released. Then, while the presence or absence of formation of a solid substance in the tube was examined by the naked eye, the amount of the solid substance formed was examined as a weight change of the tube between before and after the test. The results are shown in Table 1. In Table 1, ⊚ indicates that "the amount of the solid substance formed is less than 3 mg", ○ indicates that "the amount of the solid substance formed is from 3 to 30 mg, but there is no practical problem", Δ indicates that "the amount of the solid substance formed is from 31 to 500 mg, but there is no practical problem", and X indicates that "the amount of the solid substance formed is at least 501 mg".

Then, with respect to Ex. 8 to 10 wherein the solid substance was observed by the naked eye, the solid substance in the tube was collected and dissolved in deuterated acetone, whereupon the respective spectra of $^1$H-NMR, $^{13}$C-NMR and $^{19}$F-NMR were measured. As a result of identifying the solid substance by the attribution of peaks of the measured NMR spectra, it was a homopolymer of trifluoroethylene. This is presumed to be one formed by polymerization of trifluoroethylene.

TABLE 1

| | Oxygen concentration in gas phase (ppm by volume) | Presence or absence of solid substance | Amount of solid substance formed (mg) |
|---|---|---|---|
| Ex. 1 | 4 | ⊚ | <3 |
| Ex. 2 | 20 | ⊚ | <3 |
| Ex. 3 | 50 | ⊚ | <3 |
| Ex. 4 | 100 | ○ | 10 |
| Ex. 5 | 300 | ○ | 25 |
| Ex. 6 | 500 | Δ | 60 |
| Ex. 7 | 1000 | Δ | 100 |
| Ex. 8 | 2000 | X | 750 |
| Ex. 9 | 3000 | X | 1300 |
| Ex. 10 | 5000 | X | 2200 |

Ex. 11 and 12

In a SUS316 pressure-resistant container having an internal volume of 200 cc (maximum operating temperature: 300° C., the maximum working pressure: 20 MPa), a tube made of Pyrex (registered trademark) having the weight preliminarily measured, was inserted. The pressure-resistant container was sealed, and inside of the container was evacuated. Here, the tube was inserted to confirm the presence or absence of formation of a polymer in the pressure-resistant test container.

Then, after introducing a predetermined amount of oxygen into the pressure-resistant container, 80 g of liquefied trifluoroethylene having a purity of 99.5% was filled to bring the oxygen concentration in the gas phase to have the value shown in Table 2 at 25° C.

Then, the pressure-resistant container having trifluoroethylene thus sealed-in together with oxygen having a predetermined concentration, was placed in a hot air circulating constant temperature vessel and left to stand in a constant temperature state of 80° C. for 5 days.

Upon expiration of the 5 days, the pressure-resistant container was taken out from the constant temperature vessel, and trifluoroethylene was released. Then, while the presence or absence of formation of a solid substance in the tube was examined by the naked eye, the amount of the solid substance formed was examined as a weight change of the tube between before and after the test. The results are shown in Table 2. In Table 2, ⊚ indicates that "the amount of the solid substance formed is less than 3 mg", ○ indicates that "the amount of the solid substance formed is from 3 to 30 mg, but there is no practical problem", Δ indicates that "the amount of the solid substance formed is from 31 to 500 mg, but there is no practical problem", and X indicates that "the amount of the solid substance formed is at least 501 mg".

Then, with respect to Ex. 12 wherein the solid substance was observed by the naked eye, the solid substance in the tube was collected and dissolved in deuterated acetone, whereupon the respective spectra of $^1$H-NMR, $^{13}$C-NMR and $^{19}$F-NMR were measured. As a result of identifying the solid substance by the attribution of peaks of the measured NMR spectra, it was a homopolymer of trifluoroethylene. This is presumed to be one formed by polymerization of trifluoroethylene.

TABLE 2

| | Oxygen concentration in gas phase (ppm by volume) | Presence or absence of solid substance | Amount of solid substance formed (mg) |
|---|---|---|---|
| Ex. 11 | 4 | ⊚ | <3 |
| Ex. 12 | 200 | X | >1000 |

From Tables 1 and 2, it is seen that in Ex. 1 to 7 and 11, trifluoroethylene homopolymer being a solid product which becomes a practical problem was not observed in the liquid phase, and especially in Ex. 1 to 3 and 11, such a solid product was not observed, and it is seen that no polymerization reaction of trifluoroethylene occurred. In contrast, in Ex. 8 to 10 and 12, formation of a homopolymer of trifluoroethylene was observed. From these results, it is evident that the method of the invention is effective as a stable storage method which does not permit a polymerization reaction to take place over a long period of time.

INDUSTRIAL APPLICABILITY

According to the storage method and the storage container of the present invention, trifluoroethylene does not undergo a reaction such as polymerization, whereby it can be subjected to storage, transportation, etc. while maintaining the high quality of trifluoroethylene.

This application is a continuation of PCT Application No. PCT/JP2014/068477, filed on Jul. 10, 2014, which is based upon and claims the benefit of priority from Japanese Patent Application No. 2013-147575 filed on Jul. 16, 2013. The contents of those applications are incorporated herein by reference in their entireties.

What is claimed is:

1. A method for storing trifluoroethylene in a sealed storage container, trifluoroethylene is stored in such a state that a gas phase and a liquid phase coexist, and the concentration of oxygen in the gas phase at a temperature of 25° C. is kept to be less than 1,000 ppm by volume.

2. The method for storing trifluoroethylene according to claim 1, wherein said concentration of oxygen is kept to be from 1 to 1,000 ppm by volume.

3. The method for storing trifluoroethylene according to claim 1, wherein said concentration of oxygen is kept to be from 3 to 1,000 ppm by volume.

4. The method for storing trifluoroethylene according to claim 1, wherein said concentration of oxygen is kept to be from 3 to 300 ppm by volume.

5. The method for storing trifluoroethylene according to claim 1, wherein said concentration of oxygen is kept to be from 3 to 50 ppm by volume.

6. The method for storing trifluoroethylene according to claim 1, wherein in the gas phase, the concentration of non-condensable gases other than oxygen at a temperature of 25° C. is at most 1.5 vol %.

7. The method for storing trifluoroethylene according to claim 1, wherein an inside of an unfilled storage container is deaerated to remove oxygen in the storage container, then, liquid-state trifluoroethylene is filled and sealed, and the trifluoroethylene is stored in the sealed storage container.

8. A sealed storage container in which trifluoroethylene is filled in such a state that a gas phase and a liquid phase coexist, and a concentration of oxygen in the gas phase at a temperature of 25° C. is at most 1,000 ppm by volume.

9. The storage container for trifluoroethylene according to claim 8, wherein said concentration of oxygen is from 1 to 1,000 ppm by volume.

10. The storage container for trifluoroethylene according to claim 8, wherein said concentration of oxygen is from 3 to 1,000 ppm by volume.

11. The storage container for trifluoroethylene according to claim 8, wherein said concentration of oxygen is from 3 to 300 ppm by volume.

12. The storage container for trifluoroethylene according to claim 8, wherein said concentration of oxygen is from 3 to 50 ppm by volume.

* * * * *